United States Patent
Hamilton et al.

(10) Patent No.: US 6,184,265 B1
(45) Date of Patent: Feb. 6, 2001

(54) LOW TEMPERATURE PRESSURE STABILIZATION OF IMPLANT COMPONENT

(75) Inventors: John V. Hamilton, Foxborough, MA (US); Mary Beth Schmidt, Pomfret Center, CT (US); Keith Greer, Ft. Wayne, IN (US)

(73) Assignee: Depuy Orthopaedics, Inc., Warsaw, IN (US)

( * ) Notice: Under 35 U.S.C. 154(b), the term of this patent shall be extended for 0 days.

(21) Appl. No.: 09/362,965

(22) Filed: Jul. 29, 1999

(51) Int. Cl.$^7$ ..................................... C08F 2/46
(52) U.S. Cl. ............ 522/189; 522/157; 522/158; 522/162; 522/184; 522/911; 522/912; 528/503; 528/502 C; 528/481; 528/483; 528/499; 422/22; 422/23; 422/25; 422/32; 422/40; 422/903
(58) Field of Search .................. 522/65.71, 157, 522/158, 162, 189, 184, 911, 912, 502 C; 528/503, 481, 499; 422/22, 25, 23, 32, 40, 903

(56) References Cited

U.S. PATENT DOCUMENTS

| | | | |
|---|---|---|---|
| 4,336,618 | * 6/1982 | Raab | 3/1.913 |
| 5,037,928 | 8/1991 | Li et al. | 526/352 |
| 5,178,812 | 1/1993 | Sanford et al. | 264/171 |
| 5,270,118 | 12/1993 | Sanford et al. | 428/473.5 |
| 5,292,584 | 3/1994 | Howard et al. | 428/327 |
| 5,352,732 | 10/1994 | Howard | 524/789 |
| 5,414,049 | 5/1995 | Sun et al. | 525/333.7 |
| 5,449,745 | 9/1995 | Sun et al. | 528/483 |
| 5,468,842 | * 11/1995 | Howard, Jr. | 528/481 |
| 5,478,906 | 12/1995 | Howard, Jr. | 526/352 |
| 5,543,471 | 8/1996 | Sun et al. | 525/333.7 |

(List continued on next page.)

FOREIGN PATENT DOCUMENTS

| | | | |
|---|---|---|---|
| 373800 | 6/1990 | (EP) | A61L/27/00 |
| 446300 | 9/1991 | (EP) | A61L/27/00 |
| 701453 | 3/1996 | (EP) | A61L/27/00 |

(List continued on next page.)

OTHER PUBLICATIONS

Shen, F.W. et al., "Irradiation of Chemically Crosslinked Ultrahigh Molecular Weight Polyethylene", 34 J. Polymer Sci., 1063–1077 (1996).
Stryker Osteonics Technical Bulletin, "Crossfire™ Crosslinked Polyethylene", pp. 1–6 (Sep. 1998).
Kurtz et al. Advances in the processing, sterilization, and crosslinking of ultra–high melecular weight polyethylene for total joint arthroplasty. Biomeaterials 20 (1999) 1659–1688.*

*Primary Examiner*—James J. Seidleck
*Assistant Examiner*—Sanza L. McClendon
(74) *Attorney, Agent, or Firm*—Nutter, McClennen & Fish, LLP

(57) ABSTRACT

Wear resistance and oxidation resistance of polymer material or a polymer component for bioimplantation are improved by packaging a polymer object in a sealed gas impermeable package substantially free of oxygen, irradiating the package with penetrating radiation to an extent sufficient to effect a desired substantial level of cross-linking within the polymer, and warming the packaged object while maintaining an elevated hydrostatic pressure to cause gases released during irradiation to recombine, stabilizing the material against subsequent oxidative change. The pressure stabilization terminates active sites, substantially eliminating free radicals. When applied to finished parts, the process simultaneously hardens and sterilizes the parts without degrading mechanical properties or dimensions. When applied to bulk material or unfinished parts, the part may be subsequent machined or otherwise finished, and sterilized by any conventional means. The procedure achieves high levels of cross linking without increasing susceptibility to aging or chemical degradation.

13 Claims, 1 Drawing Sheet

U.S. PATENT DOCUMENTS

| | | | |
|---|---|---|---|
| 5,577,368 | 11/1996 | Hamilton et al. | 53/432 |
| 5,621,070 * | 4/1997 | Howard, Jr. | 528/481 |
| 5,650,485 | 7/1997 | Sun et al. | 528/483 |
| 5,684,124 * | 11/1997 | Howard, Jr. et al. | 528/481 |
| 5,728,748 | 3/1998 | Sun et al. | 522/65 |
| 5,753,182 * | 5/1998 | Higgins | 422/23 |
| 5,798,417 | 8/1998 | Howard, Jr. | 525/276 |

FOREIGN PATENT DOCUMENTS

| | | | |
|---|---|---|---|
| 722 973 * | 7/1996 | (EP) | |
| 722973 | 7/1996 | (EP) | C08J/3/24 |
| 729 981 A1 * | 9/1996 | (EP) | |
| 729981 | 9/1996 | (EP) | C08F/110/02 |
| 847765 | 6/1998 | (EP) | A61L/27/00 |
| WO9534597 | 12/1995 | (WO) | C08J/3/28 |
| WO9729793 | 8/1997 | (WO) | A61L/27/00 |
| WO 9801085 | 1/1998 | (WO) | A61F/2/00 |
| WO 98/14223 | 4/1998 | (WO) | A61L/27/00 |
| WO 98/16258 | 4/1998 | (WO) | A61L/2/08 |

* cited by examiner

LOW TEMPERATURE PRESSURE STABILIZATION OF IMPLANT COMPONENT

REFERENCE TO RELATED APPLICATIONS

This application is related to the United States patent application entitled GAMMA IRRADIATED HEAT TREATED IMPLANT FOR MECHANICAL STRENGTH and the United States patent application entitled Two STEP GAMMA IRRADIATION OF POLYMERIC BIOIMPLANT each filed simultaneously herewith on Jul. 29, 1999 by Express Mail with Express Mail Label No. EJ000510247US and No. EJ0005510255US, respectively, by the present inventors. Each of the foregoing patent applications is hereby incorporated herein by reference in its entirety.

BACKGROUND OF THE INVENTION

This invention relates to bioimplantable polymeric articles and more particularly to materials treatment methods for improving the wear resistance and oxidation resistance of such articles.

Advances in biomedical engineering have resulted in numerous polymeric articles having properties suitable for prosthetic use within the body. Polymeric components are widely used in orthopedic surgery, for example, to form articulation surfaces within artificial joints. Ultrahigh molecular weight polyethylene (UHMWPE) is an example of a polymer that is commonly used to form components of artificial joints. Among the properties required of bioimplantable polymeric components, particularly those used in artificial joints, are low friction, biocompatibility, and good mechanical properties such as surface hardness, toughness or mechanical strength, and resistance to wear and creep. Such components must also be sterile before implantation within a patient.

Some polymers and medical devices may be adversely affected by heat sterilization, so this technique is not widely used. Ethylene oxide sterilization, commonly employed for sterilizing other medical articles, may pose health or environmental risks that render this method less desirable. As a result, a preferred method of sterilizing many medical devices, including polymeric components, is by exposure to forms of ionizing radiation such as gamma ray, x-ray or electron beam radiation.

Presently, sterilization by gamma radiation is a preferred by applicant for both cross-linking and sterilizing bioimplantable polymeric components. One potential effect of gamma irradiation is that the gamma rays can initiate chemical reactions within the polymer that can affect the structure, morphology and some mechanical properties of the polymer. During gamma irradiation a variety of chemical species, such as ions, excited molecules, double bonds, oxidation products and free radicals are created within the polymer. Free radicals are believed to be a species generated during gamma radiation that may contribute most to changes in the properties of irradiated polymer.

Once free radicals are formed within a polymer, these species may participate in at least four major types of reactions. The free radicals can undergo a recombination reaction by reacting with hydrogen to eliminate the free radical, by reacting with carbon molecules to create side chains, or both. Free radicals can also initiate or participate in a chain scission reaction that results in a decrease in the molecular weight, and/or change in the density or crystallinity of the polymer, thus causing some mechanical properties of the polymer to degrade. Cross-linking is another reaction in which the free radicals can participate. Finally, the free radicals may remain trapped within the polymer material for an extended time period (e.g., years) even though not initially reacting, and thus remain available to react as conditions dictate.

The presence of oxygen in the polymeric material or in its surrounding environment can contribute to an oxidation reaction in which free radicals and dissolved oxygen react to produce a compound with a carbonyl functional group, resulting in chain scission and the creation of new free radicals. Thus, oxidation can decrease the molecular weight of a polymer (due to such chain scission), which in turn, may contribute to the degradation of its mechanical properties. Since oxygen is ubiquitous in the atmosphere and in biological fluids, this mechanism of degradation may occur whenever there remains a substantial concentration of free radicals in the irradiated polymer. Cross-linking or sterilization of polymer material or components by gamma radiation in air is believed to decrease the wear resistance of polymers due, in part, to such oxidation effects.

Since wear resistance is a key mechanical property for polymeric components that are used in joint prostheses, this problem has now been addressed by techniques such as exposure in oxygen-free environments, by subsequent removal of the affected surface layer, or other processes. Thus, one current practice addresses this problem by irradiating polymeric components in an environment of an inert gas (e.g., argon, helium, nitrogen) to minimize oxidation effects. See, Kurth, M. et al., "Effects of Radiation Sterilization on UHMW-Polyethylene" Antec 87, pp. 1193–1197 (1987); Streicher, R. K., Radiol. Phys. Chem., Vol. 31, Nos. 4–6, pp. 693–698 (1988); Streicher, R. M., "Improving UHMWPE by Ionizing Radiation Cross linking During Sterilization", 17th Annual Meeting of the Society for BioMaterials, p. 181 (1991). Others have used vacuum techniques to help purge an environment of oxygen before conducting gamma radiation sterilization. See, Yong Zhao, et al., J. Appl. Polymer Sci., Vol. 50, pp. 1797–1801 (1993), and Hamilton, U.S. Pat. No. 5,577,368.

Wear resistance is a property of great importance to artificial joint components. Natural friction within a replaced, artificial joint can cause minute particles of debris (e.g., particles from a polymer component) to become dislodged and to migrate within the joint. This phenomenon of wear debris within artificial joints is a serious problem that can inhibit the proper mechanical functioning of the joint. Wear debris can also lead to osteolysis and bone deterioration. If osteolysis develops around an artificial joint, correction typically requires surgical removal of the diseased tissue and revision of the artificial joint. Thus, to achieve good wear resistance, one must achieve material properties that limit both the amount of wear, and the nature and type of wear debris produced.

Wear resistance depends on many factors, such as the hardness and toughness of the polymer material, which may in turn depend upon specific properties such as the molecular weight of the resins, the degree of cross linking of the material, and the relative size, amount and distribution of regions of amorphous and of crystalline polymer in the microstructure of the finished material. Each of these basic properties may be altered by the application of radiation, heat or chemical agents. Moreover, the fabrication of polymer components generally proceeds from a starting material, or resin, which is provided as either a powder or granular material, or as a consolidated blank, e.g., a sheet or block or preform made from the resin, which must be machined to final form and then be sterilized after the article is fully formed. Heating and pressure, solvation or other factors involved in the consolidation step may influence underlying physical properties, and cross-linking irradiation may be necessary to sufficiently harden material into a wear-resistant solid article, either before or after final shaping. Different forms of irradiation may each have different absorption or interaction characteristics, or generate heat which further affects crystallinity or other properties of the material microstructure. Furthermore, various forms of post-processing may also be required to adjust or overcome properties altered or introduced in the forming and cross-linking stages. Thus, wear resistance depends in a rather complex way upon a number of processing steps which may be employed to treat or physically form the polymer component.

Cross-linking may be primarily effected in part by many of the same processes useful for sterilization, such as heating or irradiation of various types. In general, the radiation dose required to achieve a substantial level of cross-linking may be higher than the dosage needed for sterilization. For example, whereas a dose of 15–25 kGy is effective for sterilization, several times that level may be necessary to effectively cross link a UHMWPE component. At such levels, the evolution of chemical species and free radicals within the polymer may become significant. Moreover, while the level of cross-linking so achieved may result in substantially enhanced hardness or toughness, the irradiation may degrade mechanical properties such as the size or distribution of crystalline and amorphous regions, either immediately due to factors such as heating, or may impair the polymer properties over time as a result of the evolved species as discussed above.

Workers in the field have developed several approaches to processing the polymer material or finished parts in attempts to introduce effective levels of cross-linking while attaining suitable materials properties or rectifying processing damage. These approaches include irradiation in a vacuum, cold irradiation with subsequent melting of bulk material, chemical cross-linking and gas plasma treatment. Each of these techniques appears to enhance at least one parameter. However, the need for multi-step processing, the number of physical processes involved, and the empirical nature of evaluating actual long-term changes in the prosthesis strength and wear properties, all result in a continuing need for processes to enhance polymer strength or wear resistance.

Because excellent wear resistance is a property of such importance for polymer artificial joint components, it would be advantageous to be able to provide highly cross-linked and sterilized polymer components that have an improved and stable wear resistance.

It is thus an object of the invention to provide methods for increasing the wear resistance of a bioimplantable polymer component.

It is also an object to provide sterilization techniques for a medical grade implantable polymer component that impart or preserve important properties of the component.

A further object is to provide bioimplantable polymer component that has improved wear resistance and is less prone to the effects of oxidation.

These and other objects will be apparent to one of ordinary skill in the art upon reading the description that follows.

SUMMARY OF THE INVENTION

The invention provides a method for increasing the wear resistance of polymer parts. The method is particularly well suited to biocompatible polymer parts for use as components of artificial joints. A variety of polymer materials, particularly polyolefins such as ultra high molecular weight polyethylene (UHMWPE), can be treated according to the method of the invention to improve wear resistance and to improve oxidation resistance.

According to the method of the invention, the bulk polymer material, an unfinished component for forming a manufactured finished polymer part, or a finished component such as a bioimplantable prosthesis component, is placed within a gas impermeable and sealable package or container. The package and the material therein are then subjected to removal of surrounding oxygen by a vacuum or partial vacuum, and the package is heat sealed. Next, the package and its contents are irradiated for a period of time so as to provide a dose of radiation effective to introduce a substantial, high target level of cross-linking of the polymer that forms the part. Various forms of ionizing energy can be used to treat the material. However, the use of penetrating radiation, particularly gamma radiation and more particularly gamma radiation with an energy above 0.5 MeV, and advantageously in the vicinity of 1.25 MeV is preferred.

While the material or component is still in the packaging, it is warmed or heated above a threshold level higher than ambient but well below its melt point, and the surrounding pressure is increased substantially to between about thirty to one hundred atmospheres or more. These conditions are then maintained for a period of time such that the gas released during irradiation and trapped within the package recombines with the polymer to terminate free radicals and reduce reactivity to a low residual level. Applicant has found that this method of stabilization effectively substantially eliminates the high level of free radicals typically created by high dosage radiation cross linking treatment, and stabilizes the treated material against later oxidation. Furthermore, the treatment at a temperature below the polymer melt temperature may be carried out without introducing further cross-linking, and while maintaining dimensional stability. Following the warm/pressure treatment cycle, the material is slowly cooled, e.g., at about 5° C. per hour, down to ambient temperature. In general, the post-irradiation processing is carried out at a temperature above 30° C. and below 135° C., preferably between about 50° C. and below 120° C., and at a pressure between about 500 and 1300 psi, and these conditions are maintained for a time between four hours and seven days, with a cool down time of about four to twenty hours. With the material in a sealed gas impermeable bag, the pressure may be applied by placing the irradiated bag in a pressure chamber and filling the chamber with a pressurized fluid, such as nitrogen or other inert gas, or even a hydraulic oil. This pressure fluid may also be warmed to the desired curing temperature.

The process utilizes the gases evolved during irradiation in the closed package to terminate free radicals and stabilize the material against subsequent oxidation or scission reactions, and may avoid the degradation of basic mechanical properties typically consequent to heating, thus providing a simplified procedure for stabilizing an irradiation-cross-linked component that is suitable for commercial implementation.

Furthermore, by providing a dimension-preserving stabilization process that operates on packaged components, post-machining handling and sterilization stepsare greatly simplified.

BRIEF DESCRIPTION OF THE DRAWINGS

These and other desirable features will be understood form the description of the invention below, taken together with the drawings, wherein.

DETAILED DESCRIPTION OF THE INVENTION

Figure 1:
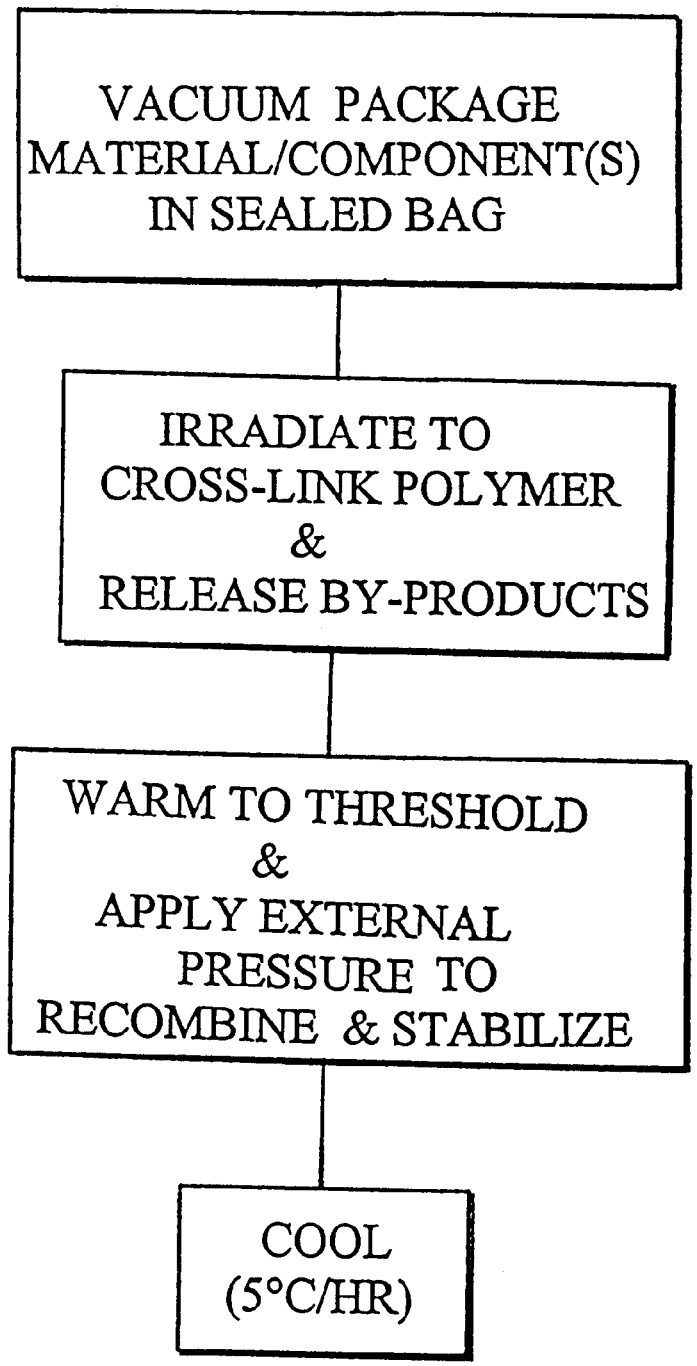
FIG. 1 is a flow chart showing steps of a method in accordance with the present invention.

The present invention provides a method for improving the wear resistance of manufactured polymer parts. According to this process the material for a desired polymer part is first consolidated from a resin or powder, and/or is formed into a billet, or machined into an unfinished or even a finished part, by known processes, such as compression molding, ram extrusion, injection molding and machining. The polymer that forms the part can be low density polyethylene, high density polyethylene, ultrahigh molecular weight polyethylene, polypropylene, polyester, nylon, polyurethane, poly(methylmethacrylate), or other biocompatible polymer typically used in biomedical applications. The preferred polymer is a polyolefin, and a most preferred polymer is UHMWPE, which is commonly used in a variety of orthopedic implants, such as liners for acetabular shells of artificial hip joints, and such as tibial bearing members in artificial knee joints. The invention will now be described with reference to a UHMWPE component.

In one embodiment, the bulk polymer material or unfinished parts that are to be subjected to the process of the invention are first placed in an isolation container such as a flexible vacuum barrier package that is formed of a gas-impermeable film and has a heat sealable opening therein. The material may take the form of sheets, pucks, rods, bars, billets or other common shape resulting from or following the consolidation process utilized on a starting resin. The unfinished part may, for example, constitute a compression molded oversize blank or a partially finished part machined from a previously consolidated blank or bulk material. When applied to a finished part the part may be a fully machined and finished component. This starting part or material will henceforth be referred to, interchangeably, as either the polymer object or the prosthesis. More than one polymer object can be placed in a single package. The package and the object are then subjected to a vacuum while the heat sealable opening remains open and the vacuum is maintained for approximately 10 seconds to 30 minutes, and preferably for about 30 seconds, after which the package is heat sealed while maintaining the vacuum, thus closing the gas impermeable package so it is at least partially, and preferably is substantially evacuated.

Thus, the packaging of the polymer object in a heat sealed package under vacuum is carried out to remove oxygen from the polymer material and from the environment within the package, and preferably also to reduce pressure within the package. The package preferably includes one or more barrier layers effective to make it impermeable to gaseous hydrogen, so that hydrogen released during a radiation treatment remains trapped in the package. Following the vacuum heat sealing of the package that contains the polymer object, the package and the object are irradiated with penetrating radiation for a period of time that is sufficient to introduce a substantial level of cross-linking of polymer chains within the polymer material. Various acceptable forms of ionizing radiation can be used to effect the sterilization of the part. These radiation forms include gamma rays, x-rays, and electron beam radiation. Gamma radiation effectively penetrates the package and material, and gamma radiation with an energy of 0.5–1.5 MeV is currently preferred.

The flexible packaging material within which the polymer parts are sealed can be selected from among many types of high barrier, flexible packaging material that are commonly used to enclose medical devices. Preferably the packaging material is a multilayered, heat seal peelable packaging material that includes a barrier layer such as a foil that is effective to block passge of hydrogen, various polymer layers and a heat seal coating. One example of a suitable material includes the following layers: polyester film-low density polyethylene-foil-ionomer-heat seal coating. Packaging materials having the following layers can also be used: polyester-low density polyethylene-foil-EAA-linear low density polyethylene-heat seal coating; and polyester-Surlyn-nylon-Surlyn-foil-EAA-linear low density polyethylene-heat seal coating. Suitable packaging materials can be obtained from a variety of sources, including Tolas Health Care Packaging of Feasterville, Pa. The thickness of the packaging material preferably is in the range of about 2 mils to 7 mils (50–175 micrometers) and is such that the vacuum foil bag readily conforms to the shape of the objects packed therein. Suitable vacuum packaging equipment for heat sealing packages under vacuum will be known to those of ordinary skill in the art. An example of a suitable vacuum packaging apparatus is a MultiVac A342 apparatus, available from Multivac, Inc. of Kansas City, Mo.

As noted above, the packaged polymer material is irradiated using penetrating radiation, preferably gamma radiation from a source such as a Cobalt 60 source. The gamma radiation is administered for a duration and at a dosage level which is effective to introduce or initiate a high and effective level of cross-linking. Thus, for example, where applicant has previously found a radiation dose of 40 kGy to introduce a sufficient level of cross-linking to meet basic standards and regulations for required implant component strength and wear characteristics, the present invention contemplates that the irradiation dosage above this range. A dosage of approximately 40–120 kGy may be used for a prosthetic component, and a dose of approximately 60–90 kGy is preferred. The irradiation dose may be delivered as gamma radiation over a time of several hours to about one day, and is most preferably delivered during about ten to fifteen hours, with the time depending on the strength of the source. As noted above, the object is preferably irradiated under substantially vacuum conditions. This has the effect that following irradiation, the gases retained within the package or container will be of relatively small amount, and are primarily the gases evolved by irradiation, principally hydrogen.

Thus, the polymer material is placed in an environment free of oxygen, and irradiated with penetrating radiation to induce substantial cross-linking. A dose of 80 kGy has been found effective to cross link a GUR 1020 material to an effective level. By effective level, is meant a level which may be somewhat above that generally used to achieve the required strength and wear properties of a commercial implant device, and preferably to a level that results insufficient hardness and toughness to have a negligible wear level.

Following irradiation, the polymer object is warmed to a threshold temperature that lies above room temperature, but well below the polymer melt point, e.g. at above 23° C. but well below melt (e.g., below 135° C. for the GUR 1020 resin UHMWPE material noted above). This may be a level of warming that promotes a limited amount of flexing of long chain molecules, without, however, introducing thermal cross-linking or even substantially affecting the diffusion of trapped or dissolved hydrogen. This slight elevation in temperature may be insufficient by itself to substantially alter the effects of radiation damage in the material. However, as a further step, while maintaining the temperature elevation, the pressure outside the sealed bag is elevated substantially, for example, to a pressure between about twenty and ninety atmospheres or more. Such thermal warming and increased pressure may be applied simultaneously, for example, by pumping a warmed pressure fluid into a pressure vessel holding the sealed vacuum barrier bag. These conditions of subcritical heating and elevated pressure are then maintained for an extended time, between four hours and seven days, such that isolated or immobilized free radicals recombine, and are terminated. The polymer is then slowly cooled from the process stabilization temperature back down to ambient at a rate of approximately 5° C./hour.

The foregoing steps of substantial radiation cross-linking followed by a low temperature, high pressure stabilization treatment preserves the dimensions of the treated polymer object, and results in a material or object which is uniformly and highly cross-linked, and has been stabilized so that it does not contain a significant level of free radicals and is not prone to degrade when subsequently stored or exposed to oxygenated environments over time. Oxidative stability is thus improved while attaining a high degree of cross-linking.

Preferably, the process is carried out on finished components, and in that case the radiation dose is effective to both cross-link and sterilize the component. The process, however, may also be applied to unfinished components or bulk material, or to components that otherwise must be removed from the packages for further processing. In that case, the components may be subsequently sterilized by any known technique. When the starting component or material is a bulk material or semifinished component, it may then be machined to form a finished prosthetic part, such as a liner or shell for an implantable prosthesis articulation component. For example, for making a liner for an acetabular cup, when material or an unfinished component has been irradiated and pressure treated as described above, it is removed from the package, machined to its final dimensions and contour. Following such machining and finishing, the finished part is then sterilized. In a preferred process, this is done by once again vacuum foil packaging the finished part and treating it with a sterilizing dose of penetrating radiation. Suitable sterilization may be obtained by exposure to gamma rays at a dose of about 20 kGy. If desired, this second dose may be of a level that is high enough to introduce a further measurable amount of cross-linking. In that case, the first stage may be carried out with a lesser dose of radiation than that required for the total level of cross-linking, and the second cross-linking step may be followed by a second stabilization or pressure-curing step. Preferably the second radiation dose is kept sufficiently low that, while effective to sterilize the component, it does not re-introduce a significant level of free radicals into the finished component. When a very low dose is planned, the bioburden of the component should be maintained at a low level during the manufacturing steps that follow the first, cross-linking and pressure stabilization, steps.

Thus, the treatment of the present invention involves packaging and irradiating the object to introduce substantial cross linking, then warming to a subcritical threshold and pressurizing the irradiated packaged object while maintaining it below melt temperature. If the object is not finished, the process may also include machining and sterilizing the treated article. In the latter case, the material or blank is stabilized in an intermediate step after substantial cross linking, allowing later steps to address sterility or to adjust the polymer mechanical properties substantially independently of the major degree of cross linking and without reintroducing any substantial level of free radicals which might ultimately degrade mechanical properties of the material.

EXAMPLE

In an exemplary embodiment of the invention, UHMWPE articles are placed in aluminum foil packages, evacuated to a pressure of approximately 20 mbar, and sealed. The packages are then irradiated with gamma rays from a Cobalt-60 source, at a high dose, above forty and up to about one hundred twenty kGy. While still packaged, the pressure is increased to more than thirty atmospheres, and temperature is raised to a treatment threshold above 50° C., but below the melt temperature. This exposes the irradiated articles to the hydrogen gas evolved during treatment, under conditions that enhance both the diffusion of hydrogen and the kinetic activity of the polymer molecules. The elevated pressure and warming is maintained for an extended time that may range, for example, from four hours to seven days, after which the material is slowly cooled, e.g., at a rate of about 5° C./hr. Lower temperatures and pressures require longer cure cycles, while temperatures up to 120° C. and pressures up to 1500 psi allowed use of a shorter cure cycle. The cured parts may then be tested to determine or confirm their oxidative stability, for example by measuring their oxidation index, which serves a measure of the level of residual free radicals present in the treated material.

The process effectively utilizes the hydrogen evolved from the initial radiation treatment to eliminate free radicals remaining in the polymer, and improves the oxidative stability of the irradiated material without increasing the degree of cross-linking. By using pressure to drive a reaction to depth within the sealed bags, handling and the mechanics of treatment are greatly simplified, and stabilization is achieved without introducing further cross-linking. The elevation of pressure may be safely and conveniently accomplished by placing the irradiated packages in a holding vessel, and pressurizing the holding vessel with a suitable gas or with an hydraulic pressure fluid. The moderate degree of warming may be applied uniformly and effectively by warming the pressure fluid, or by warming the surrounding vessel. The foil packages serve dual functions of excluding air and pressure fluid during the various steps of processing, as well as retaining the hydrogen evolved during the first stage of treatment. This small but sufficient amount of evolved hydrogen may be safely retained and the packages handled and manipulated if necessary for movement from the irradiation to the pressure treatment portions of a production line, and the retained hydrogen conveniently quenches residual radicals during the pressurized stabilization phase.

The foregoing description of the method of manufacture and the illustrative embodiments is presented to indicate the range of constructions to which the invention applies. Variations in the materials to be used to fabricate polymer samples, vacuum pressures, radiation sources, and the like, will be readily apparent to those having ordinary skill in the art. Such variations are considered to be within the scope of the invention in which patent rights are asserted, as set forth in the claims appended hereto.

The entirely of all publications and/or references noted herein are expressly incorporated by reference herein.

What is claimed is:

1. A method of preparing of a prosthetic wear surface component formed of a polymer material, such method comprising the steps of providing a polymer object packaging the polymer object in a vacuum isolation bag exposing the bag to a dose of penetrating radiation effective to substantially introduce a desired target level of cross-linking in said polymer object while evolving hydrogen, and curing the polymer object by warming the polymer object to a low temperature threshold above about 30° C. while applying external pressure above 20 bar to recombine said hydrogen and stabilize said polymer object, forming a cross linked component of enhanced oxidation resistance.

2. The method of claim 1, wherein said polymer material is a polyolefin material.

3. The method of claim 2, wherein said polymer material is an ultra high molecular weight polyethylene (UHMWPE).

4. The method of claim 1, wherein the step of exposing includes exposing to gamma radiation at an energy above 0.5 MeV.

5. The method of claim 4, wherein the polymer material is UHMWPE.

6. The method of claim 5, wherein the step of applying pressure applies hydrostatic pressure to the isolation bag.

7. The method of claim 1, wherein the step of curing is performed for a combined temperature, pressure and duration effective to terminate or link residual reactive species formed by the step of exposing to the dose of penetrating radiation.

8. The method of claim 6, wherein the step of curing includes raising to a temperature above 50° C. and below 120° C., followed by slowly cooling to ambient.

9. The method of claim 8, wherein the step of curing includes maintaining said temperature for a time between four hours and seven days.

10. The method of claim 1, wherein the step of providing a polymer object includes providing a finished prosthetic implant component.

11. A method of forming a prosthetic polymer wear surface component having enhanced oxidation resistance, such method comprising the steps of irradiating a prosthesis material or component in an isolation bag to introduce a level of cross-linking corresponding substantially to a desired material strength or hardness, wherein the step of irradiating introduces reactive species in the component curing the irradiated component to quench reactive species therein and form a stabilized irradiated component, wherein the curing is effected by warming and pressurizing the isolation bag to recombine gases released during irradiation with said reactive species.

12. A method of improving oxidative stability of an irradiated polymer implant component without increasing the degree of cross-linking induced by irradiation wherein the method is characterized by the steps of irradiating the component in a sealed container and, while still in the container, stabilizing the component by warming the component and subjecting the warm component to a hydrostatic pressure between about twenty and one hundred atmospheres or more, for a time effective to recombine evolved gases generated by the radiation with the polymer implant material.

13. An implantable prosthetic component formed of UHMWPE and being characterized by post-forming exposure to gamma radiation to introduce an effective level of cross-linking; and application of pressure to incorporate evolved gases under warm conditions and thereby terminate active species immobilized in the component such that the component is stabilized against oxidation while maintaining mechanical strength with said effective level of cross-linking.

* * * * *